United States Patent
Alving et al.

(10) Patent No.: US 6,183,416 B1
(45) Date of Patent: Feb. 6, 2001

(54) DIAGNOSTIC METHOD FOR INFLAMMATORY CONDITIONS IN THE INTESTINES

(75) Inventors: Kjell Alving, Uppsala; Jan M. Lundberg, Djursholm; Jon Lundberg; Eddie Weitzberg, both of Stockholm, all of (SE)

(73) Assignee: Aerocrine AB, Danderyd (SE)

( * ) Notice: Under 35 U.S.C. 154(b), the term of this patent shall be extended for 0 days.

(21) Appl. No.: 09/273,514

(22) Filed: Mar. 22, 1999

Related U.S. Application Data

(62) Division of application No. 08/849,282, filed as application No. PCT/SE95/01429 on Nov. 29, 1995, now Pat. No. 6,063,027.

(30) Foreign Application Priority Data

Nov. 30, 1994 (SE) .................................................. 9404161

(51) Int. Cl.[7] ...................................................... A61B 5/00
(52) U.S. Cl. ........................... 600/300; 128/898; 436/110
(58) Field of Search ............................ 128/898; 600/300, 600/301, 560, 562, 593; 514/42, 52, 492; 436/110, 116

(56) References Cited

U.S. PATENT DOCUMENTS

| | | |
|---|---|---|
| 4,412,006 | 10/1983 | Cox et al. . |
| 5,437,292 | 8/1995 | Kiphidze et al. . |
| 5,459,076 | 10/1995 | Stamler et al. . |
| 5,756,540 | 5/1998 | Lai . |
| 5,767,103 | 6/1998 | Greenberg et al. . |

FOREIGN PATENT DOCUMENTS

| | | |
|---|---|---|
| 9103243 | 11/1991 | (SE) . |
| 8803389 | 5/1988 | (WO) . |
| 9108013 | 6/1991 | (WO) . |
| 9305709 | 4/1993 | (WO) . |
| 9502181 | 1/1995 | (WO) . |

OTHER PUBLICATIONS

Loft, D. E. et al., *Lancet*, vol. 335, 1990, 1293–1295.
Holmgren Peterson, K. et al., *Scand. J. Gastroenterology* 1998:33:939–943.
Niveloni S. et al., *Gastroenterology*, Supplement, Apr. 1997, p. A391.
Frazer, A.C. et al., *Lancet*, 1959, 252–255.
Sturgess, R.P. et al., *Scand. J. Gastroenterol.* 1993; 28:760–762.
Lundberg et al., *Eur. J. Resp.*, vol. 7 (1994) 1501–1504.
Hartley et al., *J. Med. Microbiol.*, vol. 36 (1992) 96–103.
Reynolds et al., *Gasteroenterology*, vol. 108, No. 4 (1995) 902.
Boughton–Smith, *Journal of the Royal Society of Medicine*, vol. 87 (1994), 312–314.
Middleton et al., *Lancet*, vol. 341 (1993) 465–466.
Persson et al., *Lancet*, vol. 343 (1994) 146–147.
Lundberg et al, *Gut*, vol. 35 (1994) 1543–1546.
Raab, *Am. J. Gastroenterol*, vol. 87, (1992) 1453–1459.
Archer, *FASEB J.*, vol. 7, (1993) 349–360.
Moncada et al., *Pharmacol. Rev.*, vol. 43 (1991) 109–142.
Tepperman et al., *Am. J. Physiol.*, 265 (1993) G214–G218.
Whittle, Physiology of the Gastrointestinal Tract, NY:Raven Press (1994) 267–294.
Boughton–Smith et al., *Lancet*, vol. 342 (1993) 338–340.
Ji et al., *Biochem. Arch.*, vol. 5 (1989) 61–66.
Alving et al., *Eur. Resp. J.*, vol. 6 (1993) 1368–1370.
Hamid et al., *Lancet*, vol. 342 (1993) 1510–1513.
Kharitonov et al., *Lancet*, vol. 343 (1994) 133–135.

*Primary Examiner*—David J. Isabella
*Assistant Examiner*—Kelly O'Hara
(74) *Attorney, Agent, or Firm*—Birch, Stewart, Kolasch & Birch, LLP

(57) ABSTRACT

Method for diagnosis of inflammatory conditions in the intestinal canal of humans, characterized in that NO is measured in the lumen of the intestines. The NO level obtained is then compared with the level obtained for healthy individuals or with the level obtained for the same individual at another occasion. An increased level compared to the normal levels in the intestines of the healthy population is an indication of an inflammatory condition in the intestine.

5 Claims, No Drawings

DIAGNOSTIC METHOD FOR INFLAMMATORY CONDITIONS IN THE INTESTINES

CROSS REFERENCE TO RELATED APPLICATION

This application is a 37 C.F.R. § 1.53(b) divisional of U.S. Application Ser. No. 08/849,282, filed May 30, 1997 now U.S. Pat. No. 6,063,027, which is the national phase under 35 U.S.C. § 371 of PCT Application No. PCT/SE95/01429, having an International filing date of Nov. 29, 1995, which designates the United States of America. The entire contents of both of these applications are hereby incorporated by reference.

BACKGROUND OF THE INVENTION

1. Field of the Invention

The present invention relates to a new method for the diagnosis of inflammatory conditions in the intestines (i.e. small intestines and large intestines (colon and rectum)). The novelty in the method is based on our discovery that nitric oxide (NO) in intestinal gas is a clinically relevant marker for this type of inflammation.

An inflammatory condition in this part of the gastrointestinal tract may be caused by e.g. inflammatory bowel diseases like ulcerative colitis and Crohn's disease, or food intolerance like coeliac disease or food allergy, or e.g. sepsis.

2. Description of the Related Art

It is known that NO is produced at many sites in the gastrointestinal tract and believed to participate in both physiological and pathological events (Whittle G J R, Physiology of the Gastrointestinal Tract, New York: Raven Press (1994) 267–94).

A pathogenic role of NO in ulcerative colitis has been suggested, and patients with active ulcerative colitis exhibit increased mucosal NO synthesis (Middleton et al., Lancet 341 (1993) 465–66; and Boughton-Smith et al., Lancet 342 (1993) 338–40). However, the cited studies were performed in vitro and used indirect citrulline assays to measure NO-synthase activity in biopsies taken from both colonic and rectal mucosa. The studies did not account for in what layer of the intestinal mucosa the activity was located. It is likely that NO formed in the mucosa would have a tendency to diffuse towards the intestinal lumen, but in order to reach there, NO has to be produced in the superficial layers including epithelial cells, intraepithelial cells and luminal cells like e.g. phagocytes. In case this highly reactive species is produced deeper in the mucosal layer, it will be destroyed during its diffusion route. Results presented herein show for the first time that NO-synthase activity in intestinal inflammatory disease is located in the epithelial cell layer next to the lumen of the colon and rectum.

It is recognized that intestinal bacterias exist that are able to convert small amounts of nitrite to NO (Ji et al., Biochem. Arch. 5 (1989) 61–66).

With respect to the airways, alterations in NO concentrations in exhaled breathing air have been found for inflammatory conditions (Alving et al., WO 9502181; Alving et al., Eur. Resp. J. 6 (1993) 1368–70; Hamid et al., Lancet 342 (1993) 1510–13; Karithonov et al., Lancet 343 (1994) 133–135; and Persson et al., Lancet 343 (1994) 146–147. Increased levels of NO have also been found in regurgitated air (Alving et al., WO 9502181; and Lundberg et al., Gut 35 (1994) 1543–1546). A somewhat different approach for the measurement has lead to suggestions that NO in exhaled breathing air originates from the lung (Gustafsson, WO-A-9305709 and SE-A-91032433).

BRIEF SUMMARY OF THE INVENTION

The objects of the invention include diagnostic procedures for inflammatory conditions in the intestines as defined above and in particular with respect to correlation of NO production to these conditions.

We have now been successful in measuring NO concentrations in luminal gas sampled from colon and/or rectum of patients with active inflammation in the large intestine and rectum. These concentrations have been compared with those obtained from healthy control individuals.

Our finding is that the NO levels are increased in case of inflammatory conditions of the intestine. The expression "healthy individuals" means individuals with uninflamed intestinal mucosa.

Accordingly, the inventive method is characterized by the following steps:
  obtaining a gas sample from the lumen of the intestines of an individual;
  determining its content of nitric oxide (NO);
  comparing the found level with the level obtained for healthy individuals or with the level obtained for the same individual at another occasion.

An increased level relative the level of healthy individuals is an indication of an inflammatory condition in the intestines of the individual from which the sample was obtained. In case the level is compared with a level at another occasion, e.g. an earlier occasion, and found to be increased, this is an indication of a worsening of the inflammatory condition. Correspondingly, a decreased level means improvement. The sampling and measurement techniques should of course be essentially the same for values to be compared.

The sample is preferably obtained after the intestinal lumen concerned has been emptied, but such a procedure may not be necessary. The methods works in spite of the fact that the intestines can never be totally cleared from bacteria. The sample may be taken through catheters placed in e.g. the colon and equipped with syringes for collecting the gas, for instances during colonoscopy (colonoscopes are normally equipped with canals allowing withdrawal of gas samples from the intestinal lumen). Samples may also be taken with the same type of instrument as described by Raab et al. (Am. J. Gastroenterol. 87 (1992) 1453–1459). See also Krog et al., (WO-A-108013). With respect to rectum, gas samples may be directly collected for instance by aspirating rectal gas into a syringe. Samples may also be taken from the lumen of the small intestines, by using e.g. the equipment described by Odlind et al (EP-A-455,368). The methodologies presented by both Raab et al and Krog et al provide the possibility of obtaining samples representative for segments of colon and rectum.

The NO content may be determined/calculated as a concentration value, absolute amount or relative some internal or external standard. The content may be expressed as values normalised against components that natively are present in intestinal gas together with NO, preferably in fairly constant levels (internal standards). The NO content may also be calculated as amount secreted per time unit when taking air flow into account. When using balloon techniques as described by Krog et al., (WO-A-108013) and Odlind et al (EP-A-455,368) the amount found may be taken in relation to exposed mucosal area. The local NO-production may be increased by administering the substrate L-arginine perorally, intravenously, or locally e.g. via the colonoscope to enable the detection of low grade inflammation.

For out-patient sampling of intestinal air, rectal samples are preferred (although this does not exclude other type of sampling for this type of patients). Rectal sampling results in NO values which measure both rectal and colonic inflammation in case gas is allowed to freely spread in the intestinal canal. By using the techniques described by Krog et al., (WO-A-108013), NO values which measure rectal inflammation may be obtained.

Methods for the determination of NO in gas samples are well-known in the field. Due to the low levels concerned, NO gas analyzers based on chemiluminescent detection is preferred at the priority date. See for instance Archer, FASEB J., 7 (1993) 349–60 and Alving et al., WO 9502181.

DETAILED DESCRIPTIONS OF THE INVENTION

Ulcerative Patients

During colonoscopy, luminal gas was aspirated (60 cl over a period of 5 sec) from different parts of the colon and rectum through a thin catheter into a syringe in 6 patients with active ulcerative colitis (aged 27–48, mean 38) and from 12 control patients with uninflamed mucosa (aged 26–68, mean 59) who were undergoing colonoscopy because of suspected malignancy or polyps. Inflammation was confirmed histologically in each patient. Two of the patients with ulcerative colitis were taking corticosteroids and salicylates perorally, two were taking salicylates alone, and the remaining two patients were not under any medication at the time of study. Routine preparations before colonoscopy, including water enema and ingestion of isotonic polyethylene glycol (Laxabone®, TIKA, Lund, Sweden), were performed in each subject.

Aspirated gas was immediately injected into a chemiluminescence NO analyzer (CLD 700, ECO Physics, Dürnten, Switzerland) and peak levels of NO were registered. The detection limit for NO was one part per billion (ppb) and the analyzer was calibrated at known concentrations of NO in $N_2$, using an electromagnetic flow controller (Environics Inc, Middleton, CT, U.S.). The NO values remained stable in the syringe for more than 3 minutes at widely different concentrations (5–25,000 ppb) of NO. The chemiluminescence assay is highly specific for NO and there is no interference from other nitrogen oxides (Archer, FASEB J. 7 (1993) 249–60). NO levels in ambient air were under 4 ppb. The Mann-Whitney U test was used for the unpaired comparisons.

Intraluminal NO levels in the colon were more than 100 times higher (p=0.0001) in patients with ulcerative colitis (7741±1910) than in controls (45±7) when calculating individual levels as the mean $V_f$ for different sites in the colon (sigmoid, left, transverse and right colon). The separate means for the different sites in the colon and rectum are shown in the table.

TABLE

Mean NO concentrations in luminal gas sampled at different levels of the large intestine in controls and patients with ulcerative colitis (UC).

|  | Controls (n = 12) | UC (n = 6) |
| --- | --- | --- |
| Rectum | 27 | 2125 |
| Sigmoideum | 32 | 3912 |
| Left colon | 46 | 10125 |
| Transverse colon | 71 | 10475 |
| Right colon | 65 | 10900 |

There was no overlap between the two groups for any of the two sites. In patients with active ulcerative colitis, NO concentrations were increased in the entire colon. Although the highest concentrations were seen in gas sampled from the most severely inflamed areas, NO levels were significantly elevated also in parts of the colon that showed no signs of inflammation. Luminal NO concentrations in ulcerative colitis patients treated with corticosteroids or salicylates were also markedly increased compared to those in controls, and did not differ from those in unmedicated ulcerative colitis patients.

Crohn's Disease

In two patients with active Crohn's disease, colonic NO levels of approximately 1000 ppb were noted using the same technique as described above. Thus, this disease seems to exhibit intermediate levels of NO in colonic gas.

Immunohistochemistry for NO Synthase

During colonoscopy of controls and patients with IBD, a mucosal biopsy was taken to immunohistochemically determine the presence and location of NO synthase. Briefly, intestinal mucosal tissue samples were, after fixation and freezing, cut into 14 $\mu$m thick sections. The presence of inducible NO synthase was determined using a rabbit polyclonal antiserum that stains the inflamed bronchial epithelium of asthmatics but not controls (Hamid et al., Lancet 342 (1993) 1510–1513). For visualization a goat-anti-rabbit-IgG-antibody conjugated with the fluorescent matter FITC was used. By the aid of this method inducible NO synthase was found only in the intestinal epithelium of patients with ulcerative colitis and Crohn's disease, but not in the controls. However, the staining was patchy and could not be found in all specimens.

Discussion

NO found in luminal gas is likely to be produced in the colonic mucosa, as NO-synthase activity has been described there (Boughton-Smith et al., Lancet 342 (1993) 338–340). At this stage it cannot be excluded that some of the luminal NO might be of bacterial origin, since some strains of bacteria are able to produce NO from nitrite (Ji et al., Biochem. Arch. 5 (1989) 61–66). However, in this study, bacteria are not likely to be a major NO source, since all patients were carefully prepared before colonoscopy and no faecal matter was seen. A more common property of bacteria is the ability to reduce nitrate to nitrite. Furthermore, both nitrate and nitrite are common constituents of food stuff. Therefore nitrite and nitrate are not specific markers for local NO production in the intestine. The high NO concentrations found in luminal gas sampled from uninflamed areas in patients with inflamed large intestine are probably due to the fact that in colitis, the colon is relaxed and distended: the different parts of the colon communicate and the intestinal gases are uniformly distributed.

It is a well known problem that histological analysis of inflammation in a biopsy from the intestinal mucosa may not be representative for the general inflammatory state. Since NO in gas will be more evenly distributed, this method may correlate better with disease, i.e. the area of inflamed mucosa together with the degree of inflammation in affected areas. The lower levels of NO in Crohn's disease may be an example of this, since normally a larger area of the epithelial lining is affected in the ulcerative colitis compared to Crohn's disease. Both direct measurements of NO in the intact colonic lumen and indirect measurements of NO-synthase activity in whole mucosa (Middleton et al., Lancet 341 (1993) 465–66; and Boughton-Smith et al., Lancet 342 (1993) 338–40) indicate that NO production is much larger in patients with inflammatory conditions in the intestine than in controls.

However, the difference between NO production in the two ulcerative colitis patients appeared much larger when the direct luminal method was used (100 times compared to 4–8 times). Furthermore, no increased NO-synthase activity was seen by the indirect method in patients with Crohn's disease, whereas our direct method showed approximately 20 times increased levels of luminal NO. When measuring NO production in whole mucosa using the indirect method, normal NO production from all layers of the mucosa will contribute, thus increasing background levels and reducing the differences between the groups. Luminal NO measurements, on the other hand may reflect NO production only in the most superficial parts of the mucosa, as NO produced in the deeper mucosal structures will be trapped by e.g. haemoglobin in mucosal blood vessels and therefore will not reach the lumen. Consequently, this suggests that the NO production detected in luminal gas in inflammatory conditions is mainly located to very superficial mucosal layers. Thus NO gas measurements in the intestines may be a sensitive measure of inflammation, since NO production should not take place at all in the normal epithelium.

Active ulcerative colitis is associated with an increase in the activity of inducible NO synthase. This apparently does not fit with the classical view of inducible NO synthase as being steroid sensitive (Moncada et al., Pharmacol. Rev. 43 (1991) 109–141), since in our study and in an earlier study (Boughton-Smith et al., Lancet 342 (1993) 338–40), patients treated with corticosteroids did not differ from untreated as far as NO production was concerned. Whether this reflects an incomplete penetration of steroids to NO-producing cells in the mucosa or the presence of a steroid resistant inducible NO synthase remains to be studied. In our study, salicylates did not seem to interfere with NO production either. However, it should be pointed out that all patients on treatment with salicylates suffered from an acute exacerbation of ulcerative colitis despite ongoing treatment. Thus, we cannot tell whether salicylates interfere with NO synthesis in other ulcerative colitis patients where treatment is more successful and no activation of colitis occurs. Since the treatment have apparently failed in these patients with acute symptoms and high NO levels, measurements of intestinal NO may be useful in the testing of new drugs.

It still remains unclear whether an increased NO production seen in patients with an inflammatory condition in the intestine is beneficial or harmful for the tissue. NO or subsequent reactive products may have cytotoxic actions against host cells when produced in excess (Tepperman et al., Am. J. Physiol. 265 (1993) G214–G218). On the other hand, large concentrations of luminal NO are normally present in e.g. the nasal airways (Lundberg et al., Eur. J. Resp. 7 (1994) 1501–1504) and the stomach (Lundberg et al., Gut 35 (1994) 1543–1546) without causing local tissue damage. Moreover, NO has been suggested to play an important role in host defence mechanisms, e.g. by its bacteriostatic properties (Moncada et al., Pharmacol. Rev. 43 (1991) 109–141). This is supported by the previous finding that patients with active ulcerative colitis exhibit a reduced number of bacteria in the rectal mucosa compared to patients with inactive disease and to controls (Hartley et al., J. Medical. Microbiol. 3.6 (1992) 96–103.

What is claimed is:

1. A method for diagnosing food intolerance in a human, comprising the steps of:

obtaining a gas sample from the lumen of the intestines of the human;

measuring the level of nitric oxide in the gas sample;

comparing the measured level with the expected level for a healthy human or with a prior level measured in the human; and diagnosing the presence or absence of food intolerance using the results of said comparison.

2. The method according to claim 1, wherein the sample is taken from the lumen of the rectum.

3. The method according to claim 1 or 2, wherein an increased level of nitric oxide indicates coeliac disease.

4. The method according to claim 1 or 2, wherein an increased level of nitric oxide indicates food allergy.

5. The method according to claim 1 or 2, wherein an increased level of nitric oxide indicates lactose intolerance.

* * * * *